United States Patent [19]

Thomis

[11] Patent Number: 4,662,378
[45] Date of Patent: May 5, 1987

[54] DEVICE FOR MONITORING BODY SIGNALS

[76] Inventor: Wendl Thomis, 132 Coburn Woods, Nashua, N.H. 03063

[21] Appl. No.: 666,359

[22] Filed: Oct. 30, 1984

[51] Int. Cl.⁴ .............................................. A61B 5/04
[52] U.S. Cl. ..................................... 128/644; 128/696
[58] Field of Search ............... 128/644, 799, 802, 690, 128/687, 639, 640, 641, 903, 696, 708, 695

[56] References Cited

U.S. PATENT DOCUMENTS

| | | | |
|---|---|---|---|
| D. 256,560 | 8/1980 | van Eyben | D10/30 |
| 631,733 | 1/1899 | Bonfils et al. | 128/802 |
| 3,480,010 | 11/1969 | Crossley | 128/802 |
| 3,717,141 | 2/1973 | Krohn et al. | 128/644 |
| 4,052,979 | 10/1977 | Scherr et al. | 128/690 |
| 4,069,955 | 1/1978 | Noyes | 128/903 |
| 4,216,779 | 8/1980 | Squires et al. | 128/708 |
| 4,224,948 | 9/1980 | Cramer et al. | 128/690 |
| 4,273,135 | 6/1981 | Larmore et al. | 128/640 |
| 4,494,950 | 1/1985 | Fischell | 128/903 |

Primary Examiner—William E. Kamm
Attorney, Agent, or Firm—Lahive & Cockfield

[57] ABSTRACT

A necklace device has two skin electrodes mechanically tethered to it at relatively widely separated locations to detect the wearer's heart beat or another body signal. The electrodes are electrically connected, by the necklace itself or by conductors which it conceals, to circuitry in a pendant or other necklace ornament. The pendant circuit processes the body signal and may store it, display information obtained from it or transmit it to a separate receive and processing/display element.

11 Claims, 2 Drawing Figures

DEVICE FOR MONITORING BODY SIGNALS

This invention relates to a jewelry-like device for monitoring body activity electrically. In particular it provides such a device for providing continuous monitoring during everyday activity.

A common instrument which monitors electrical signals produced by human body activity is the electrocardiograph. An electrocardiograph obtains data regarding human activity from electrodes in contact with the skin at relatively widely separated body locations. A wide spacing is desired between the electrode locations to sense a relatively large electrical potential difference as the heart beats.

The continuous placement of electrodes on a person for prolonged periods, especially during various life activities, is often desired for cardiac analysis and study. Various straps, harnesses and other structures have been devised to provide this placement of electrodes, as illustrated by the disclosures in U.S. Pat. Nos. 4,301,808; 4,120,294; 4,052,979; and 3,442,263. These structures however have numerous shortcomings. Some are unsightly, and others are cumbersome, inconvenient or uncomfortable to wear during everyday activities.

An object to this invention is to provide a device for monitoring human body electrical signals which is comfortable and convenient for prolonged use during everyday activities. It is a further object that the device be attractive in appearance. Another object is to provide such a device that can provide the user with heart rate and other body activity information in a prompt easily intelligible and convenient manner.

A particular object is to provide a device for monitoring body signals from relatively distal locations on the body and which is convenient for prolonged use during everyday activities and yet which is ornamental.

Other objects to the invention will be apparent from the following description.

SUMMARY OF THE INVENTION

A body-monitoring device according to the invention has a loop-like necklace element and has two electrodes that are mechanically tethered to the necklace element at relatively widely spaced body locations. Each electrode can contact the skin for sensing an electrical body signal, such as the electrical potential difference associated with the heart beat. The device includes electrical conductor elements incorporated into the necklace element and for electrical connection between the electrodes and an electrical circuit which responds to the sensed signal. The incorporation of the conductor elements into the necklace element conceals them for a decorative, ornamental appearance.

In a preferred embodiment, one electrode is located along the necklace element for contact with the skin on the vertebrate bone at the back of the neck. The other electrode is located along the necklace for contact with the skin near the center of the breast. An alternative is that the two electrodes be located along the necklace for contact with the skin on opposite sides of the neck either above or on the breastbones. In both embodiments, the necklace element disposes the electrodes substantially diametrically opposite one other relative to the loop configuration of the necklace element and hence with maximal separation.

Another preferred feature is that the device include a necklace ornament such as a pendant which houses the electrical circuit for responding to the sensed electrical signal. The circuit can include elements for the wireless transmission of an electrical signal responsive to the sensed electrode signal to a receiving unit separate from the necklace. This separate receiver can also be a personal ornamental device, such as a wristwatch-like device, for wearing on the body. The receiver unit can include circuit elements for receiving the transmitted electrical signal and for processing and storing it, and for displaying and otherwise indicating information about the body, as sensed with the electrodes.

The invention thus provides an ornamental necklace device which spans between two widely spaced body locations and which supports electrodes at those locations. The necklace element connects the electrodes to a circuit which the necklace carries and which responds to body signals sensed by the electrodes. The device is well suited for prolonged wearing for monitoring body conditions under various life activities. Further, it is attractive and ornamental in appearance, as well as being relatively light and comfortable to wear.

The invention accordingly comprises a device embodying features of construction, combinations of elements, and arrangements of part as explained in the following detailed disclosure, and the scope of the invention is indicated in the claims.

BRIEF DESCRIPTION OF DRAWINGS

Other objects, features and advantages of the invention will be apparent from the following description of preferred embodiments, including the drawing in which.

DESCRIPTION OF PREFERED EMBODIMENTS

Figure 1:
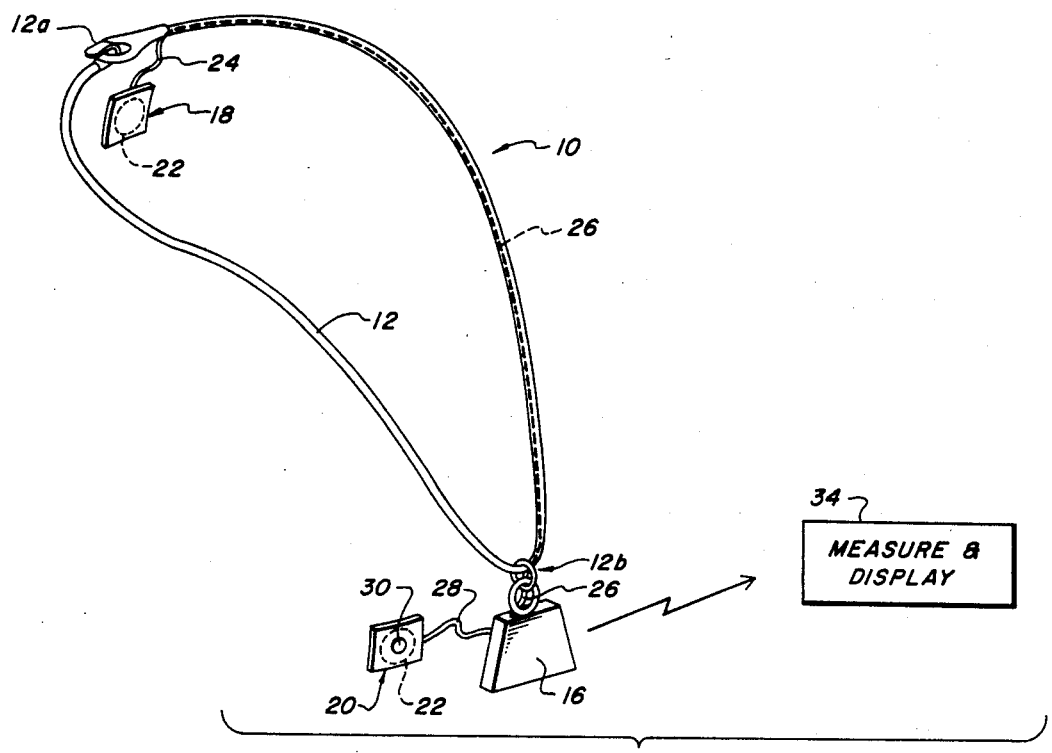
FIG. 1 shows an ornamental necklace device according to the invention for the nonintrusive monitoring of human body electrical signals.

FIG. 1 shows that a first device 10 according to the invention is in effect a necklace which a person can wear loosely about the neck. As shown, the necklace has a neckstrand 12 of any desired ornamental form. Preferably the strand 12 is a form a light weight quality jewelry which is attractive and comfortable to wear. The illustrated necklace has a clasp 12a at the upper back end, as is conventional.

At the lower front end 12b, the neckstrand carries a pendant 16, which also preferably is fashioned as a jewelry ornament.

Two skin electrodes 18 and 20 are attached to the neckstrand 12. The electrodes 18 and 20 are typically small, soft, skin colored discs with metal contacts, typically of silver or silver chloride alloy, as conventional. Each electrode attaches to the skin, for electrical contact, with a surgical grade electrically conductive adhesive 22, as conventionally used.

The electrode 18 is located along the neckstrand 12 adjacent to the catch 12a so that it may be fastened to the skin of the wearer at the back of the neck over a vertebrate bone. The electrode 18 is connected mechanically to the necklace by a short tether 24. The tether 24 preferably is a chain or other like ornamental strand. Electrode 18 may alternatively be an integral part of clasp 12a and thus require no tether.

The illustrated pendant 16 is hung at the normal central front location on the neckstrand so that it will be located, when worn, near the center of the breast. An electrical connection is made between the neck electrode 18 and the pendant 16 by way of the tether 24 and the neckstrand 12. The conductive path can be provided by the neckstrand 12 itself or it can be provided by a separate insulated wire woven into or through or otherwise decoratively incorporated into the structure of the neckstrand. In the embodiment of FIG. 1, the conductive path is a separate insulated conductor 26 which extends continuously from the contact of the electrode 18 along the tether 24 and the neckstrand 12 to the necklace links that suspend the pendant 16, and which feeds into the pendant.

The other electrode 20 is located along the neckstrand 12 so that it may be fastened to the skin over the breastbone, preferably centered between the pectorals, approximately six inches below the Adam's apple and directly beneath the pendant 16.

A second tether 28 provides both mechanical and electrical connection between the second electrode and the pendant 16. The second tether 28, an illustrative example of which is a short gold or like conductive metal chain, attaches at one end to the electrode 20 and at the other to the pendant 16. The pendant 16 is then allowed to dangle naturally within the limits of the tether 28. Thus, the second tether 28 can hold the pendant 16 close to the breast to limit movement during various activities. The breast electrode 20 may, as FIG. 1 illustrates, carry on the outer side a fastener 30, such as a hook-and-loop fastener, to attach to a mating fastener on the pendant 16 and thereby hold the pendant firmly to the breast. The second tether 28 may carry a separate insulated wire for electrically connecting the breast electrode 20 to the circuitry within the pendant 16. As a further alternative, the second tether may feed from the pendant 16 to the neckstrand 12, and then span off to the breast electrode 20.

With further reference to FIG. 1, the illustrated pendant 16 houses an electrical circuit of a known design and construction for responding to the electrical signal received from the electrodes 18 and 20. For example, the pendant circuit may include a preamplifier and an FM transmitter, both powered by a battery within the pendant. The amplifier receives and amplifies the electrical signal from the electrodes and the transmitter broadcasts it to a separate measure and display unit 34. The measure and display unit receives the transmitted signal, and provides demodulation, processing and storage of the signal as appropriate for the measurements or the processing to be made, all in a manner and with circuitry well-known to those skilled in the art. The unit 34 also includes conventional elements for displaying or otherwise indicating information about the wearer, such as the heartbeat. The unit 34 can also include a memory element for storing the electrode signals it receives, for subsequent off-line analysis and processing by other equipment.

In one illustrative form of the device shown in FIG. 1, the neckstrand 12 with the electrodes 18, 20 and circuit-housing pendant 16 continuously monitors a person's heart activity to provide an extensive cardiac data base. The cardiac database can be stored and processed in the measure and display unit 34. The processing in the measure and display unit 34 of the resulting signals uses known methods and circuits. One example of such processing, aside from medical health care, is for the measure and display unit to compute a caloric consumption rate by measuring the level of the heart rate above a resting rate. In another example, the processor measures cardiovascular fitness. For this purpose the measure and display unit 34 measures and compares the heart pulse rate during various activities.

Another illustrative operation is for the device to store a selected cardiac rate and to produce a perceptable signal when the heart rate of the wearer attains that rate. The device moreover can signal when the desired heart rate is achieved and maintained for a selected time. The device can also measure cardiac recovery time, and grade it, according to norms stored in a memory in either the measure and display unit 34 or within the pendant 16. Thus, the necklace-like device 10 facilitates the continuous monitoring of a person's heart throughout varied body activities, and thereby enables various kinds of information to be stored, processed, and displayed.

Figure 2:
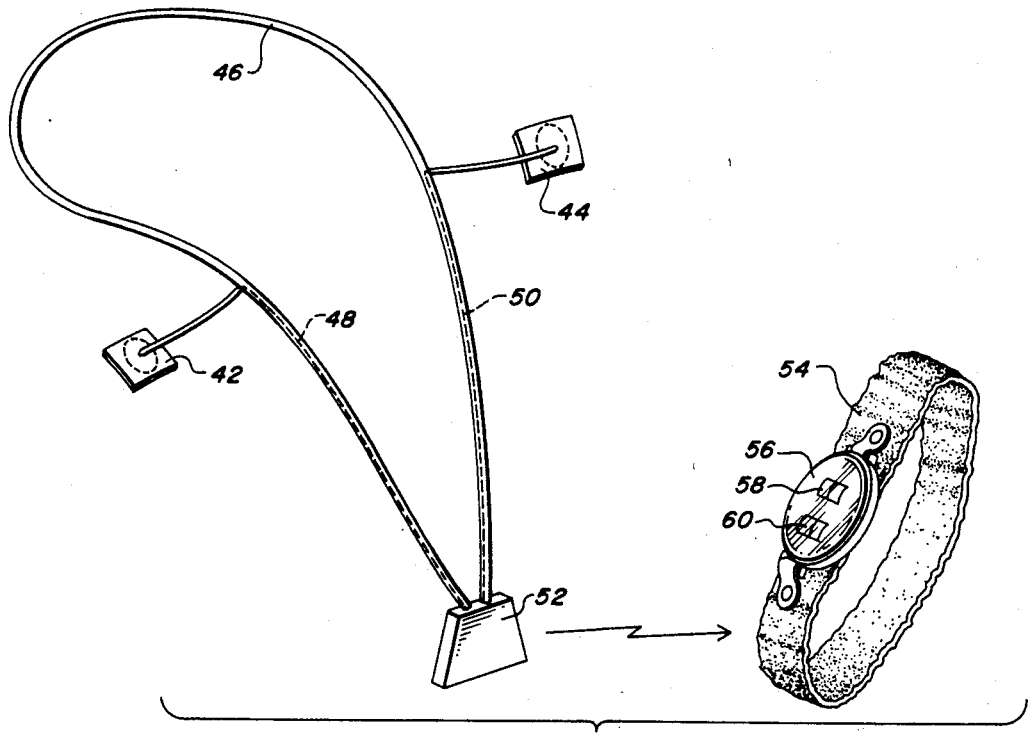
FIG. 2 shows another embodiment of the invention.

FIG. 2 shows another nonintrusive necklace-like device according to the invention for monitoring electrical signals produced by human body activity. In this embodiment, two electrodes 42 and 44 are located on either side of a necklace 46 so that they may be fastened to the body of the wearer on opposite sides of the neck. Two electrically isolated wires 48 and 50 are incorporated in the necklace 46 to conduct signals from the two electrodes to the electrical circuitry within a pendant 52 which the necklace 46 supports.

The device of FIG. 2 further illustrates that the measure and display device can be incorporated into a device like a wristwatch 54. The wristwatch 54 accordingly includes electrical circuits for receiving signals transmitted via electromagnetic radiation from the pendant 52 and for providing the desired signal processing, storage, recording and display. The illustrated wristwatch includes a conventional time display 56 and a display 58 of pulse rate information or other cardiac or body activity information as sensed with the electrodes 42 and 44.

The invention described above accordingly provides an ornamental device for wearing on the human body in a suspended manner and which attaches electrodes from widely spaced body locations, between which the device spans, to a circuit which the device carries and which responds to the body signals which the electrodes sense. In addition to the loop element and the two electrodes, the device can have an ornament which houses electrical circuitry for responding to the signals which the electrodes sense. The circuitry can provide complete processing and produce output information responsive to the signals. Alternatively, it can store the sensed signals for subsequent off-line processing, or it can transmit the signals to a separate receiving and measurement unit.

It will be apparent to those skilled in the art that additions, subtractions and modifications of the invention as shown and described in the illustrated embodiments, other than those noted, can be made by those skilled in the art within the spirit and scope of the invention, as set forth in the following claims.

Having described the invention, what is claimed is new and secured by Letter Patent is:

1. A personal ornamental device for monitoring body signals, such device comprising
   a necklace loop for hanging loosely about the neck, said loop incorporating electrically conductive means for electrical connection to each of first and second electrodes,
   a first and second electrode engaging means for mechanically engaging the said electrodes, said first and second engaging means being located at diametrically opposing positions about said loop, a housing carried by the loop, signal means within the housing for receiving electrode signals through said conductive means and for developing an output indicative of body signals, at least one said engaging means being attached to at least one of said loop and said housing so as to anchor the loop in a substantially fixed orientation about the neck when engaged with a said electrode adhered to the skin.

2. A device according to claim 1 in which said loop includes an ornamental feature defining a normal orientation of the loop about the neck, such that said engaging means are located near a vertebrate bone at the back of the neck, and near the center of the breast.

3. A device according to claim 1 in which said loop includes an ornamental feature defining a normal orientation of the loop about the neck, such that said engaging means are located on opposite sides of the neck.

4. A device according to claim 1 in which said conductive means comprises an electrical conductor for electrical connection to at least one of said first and second electrodes.

5. A device according to claim 1 in which said loop means includes pendant means and electrical circuit means housed in said pendant means for responding to the electrical signal sensed by said first and second electrodes.

6. A device according to claim 5 in which said electrical circuit means further includes means for transmitting said sensed electrical signal to a receiver separate from said loop element.

7. A device according to claim 6 further including a second personal ornamental device for wearing on the body, and means located within said second device for receiving, storing and processing said transmitted electrical signal.

8. A device according to claim 7 wherein said second personal ornamental device includes an ornamental housing having said means for receiving, storing and processing located therein, said housing further including means for mounting on a wristband.

9. A device according to claim 8 further including means for indicating information about the condition of the heart generated by said receiving, storing and processing means, and housed in said second personal device, and wherein said indicating means includes timing means for providing time information.

10. A necklace-like device for the non-intrusive monitoring of human body electrical signals, said device comprising first and second electrode means for placement on the body skin, a necklace, electrical circuit means carried by said necklace and operative in response to body electrical signals sensed by said electrode means for developing an output representative thereof, means forming first and second electrical conductor means interconnecting said circuit means and said first and second electrode means, respectively, for placing said electrode means in circuit with said circuit means, said first conductor means extending along said necklace and concealed therewith from said circuit means to a first body location where it connects to said first electrode means so as to anchor the necklace thereto, said second conductor means extending from said circuit means to a second body location where it connects to said second electrode means, said second location being distal along said necklace and on said body from said first location.

11. A necklace-like device according to claim 10 further comprising a necklace ornament element carried on said necklace and housing said electrical circuit means therewithin.

* * * * *